US012806238B2

(12) United States Patent
Asaoka et al.

(10) Patent No.: US 12,806,238 B2
(45) **Date of Patent: *Nov. 24, 2026**

(54) PROPHYLACTIC AGENT FOR BRAIN ATROPHY, METHOD FOR PREVENTING BRAIN ATROPHY, CULTURE, USE OF CULTURE, FOOD OR BEVERAGE, FOOD FOR PREVENTING BRAIN ATROPHY, SUPPLEMENT FOR PREVENTING BRAIN ATROPHY AND MEDICINE FOR PREVENTING BRAIN ATROPHY

(71) Applicant: MORINAGA MILK INDUSTRY CO., LTD., Tokyo (JP)

(72) Inventors: Daisuke Asaoka, Tokyo (JP); Toshifumi Okusa, Tokyo (JP); Nobuhiro Sato, Tokyo (JP); Kazuya Ono, Zama (JP); Kanetada Shimizu, Zama (JP); Noriko Katsumata, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 287 days.

This patent is subject to a terminal disclaimer.

(21) Appl. No.: 18/700,380

(22) PCT Filed: Oct. 21, 2022

(86) PCT No.: PCT/JP2022/039307

§ 371 (c)(1),
(2) Date: Apr. 11, 2024

(87) PCT Pub. No.: WO2023/068363

PCT Pub. Date: Apr. 27, 2023

(65) Prior Publication Data

US 2025/0000917 A1 Jan. 2, 2025

(30) Foreign Application Priority Data

Oct. 22, 2021 (JP) ................................ 2021-173451

(51) Int. Cl.
*A61K 35/745* (2015.01)
*A61P 25/28* (2006.01)

(52) U.S. Cl.
CPC ............ *A61K 35/745* (2013.01); *A61P 25/28* (2018.01)

(58) Field of Classification Search
CPC combination set(s) only.
See application file for complete search history.

(56) References Cited

U.S. PATENT DOCUMENTS

| | | | |
|---|---|---|---|
| 10,980,849 B2 | 4/2021 | Kobayashi et al. | |
| 2010/0284979 A1 | 11/2010 | O'Mahony et al. | |
| 2012/0171165 A1 | 7/2012 | Buck et al. | |
| 2012/0171167 A1 | 7/2012 | Kondo et al. | |
| 2015/0297584 A1 | 10/2015 | Tsuruoka et al. | |
| 2019/0083549 A1 * | 3/2019 | Kobayashi ............. | A23L 33/10 |
| 2020/0377961 A1 | 12/2020 | Van Sinderen et al. | |
| 2023/0218686 A1 | 7/2023 | Shimizu et al. | |

FOREIGN PATENT DOCUMENTS

| | | | |
|---|---|---|---|
| CN | 103402524 | A | 11/2013 |
| CN | 109568429 | A | 4/2019 |
| CN | 110691592 | A | 1/2020 |
| EP | 2289505 | A1 | 3/2011 |
| EP | 2478910 | A1 | 7/2012 |
| EP | 3466435 | A1 | 4/2019 |
| JP | 2014-009214 | A | 1/2014 |
| JP | 2014-101324 | A | 6/2014 |
| JP | 6853821 | B2 | 3/2021 |
| KR | 10-2012-0043111 | A | 5/2012 |
| WO | WO2011/034166 | A1 | 3/2011 |
| WO | WO2011/114916 | A1 | 9/2011 |
| WO | WO2014/070016 | A2 | 5/2014 |
| WO | WO2016/065419 | A1 | 5/2016 |
| WO | WO2017/209156 | A1 | 12/2017 |
| WO | WO2021/256077 | A1 | 12/2021 |

OTHER PUBLICATIONS

Sinitsyn, V. E., et al., "The Role of Methods for Quantitative Analysis of Magnetic Resonance Imaging Data in the Diagnosis of Alzheimer's Disease at an Early Stage," Literature Reviews. Bulletin of Roentgenology and Radiology 2017;98(5):269-274, with English language machine translation.
Official Action for Russian Patent App. No. 2024110425 (Mar. 12, 2025) with English language translation thereof.
Toshiaki Ishii et al., "Oral Administration of Probiotic Bifidobacterium breve Improves Facilitation of Hippocampal Memory Extinction via Restoration of Aberrant Higher Induction of Neuropsin in an MPTP-Induced Mouse Model of Parkinson's Disease", Biomedicines, vol. 9, No. 2, Article. 167, 2021.
Extended European Search Report for European Patent App. No. 22883665.6 (Sep. 25, 2025).
Office Action from Japanese Patent App. No. 2021-173451 (Sep. 30, 2025)—English language translation.
International Search Report for PCT Patent App. No. PCT/JP2022/039307 (Dec. 13, 2022).
Xiao, J., et al., "Probiotic Bifidobacterium breve in Improving Cognitive Functions of Older Adults with Suspected Mild Cognitive Impairment: A Randomized, Double-Blind, Placebo-Controlled Trial," J. Alzheimer's Dis. 2020;77 (1):139-147.

(Continued)

*Primary Examiner* — Jennifer E Graser
(74) *Attorney, Agent, or Firm* — Cermak & McGowan LLP; Shelly Guest Cermak

(57) ABSTRACT

The brain atrophy suppressor contains, as an active ingredient, a culture containing *Bifidobacterium breve* MCC1274 (FERM BP-11175) for administration to a subject selected from a healthy individual, an individual diagnosed with mild cognitive impairment, an individual assessed as having cognitive decline and a subject at a risk of a neurodegenerative disease.

3 Claims, 2 Drawing Sheets

(56) References Cited

OTHER PUBLICATIONS

Bernier, F, et al., "Association of Plasma Hemoglobin A1c with Improvement of Cognitive Functions by Probiotic Bifidobacterium breve Supplementation in Healthy Adults with Mild Cognitive Impairment," J. Alzheimer's Dis. 2021;81(2):493-497.

Office Action from Russian Patent App. No. 2024110425 (Oct. 28, 2024) with English translation.

Maehata, Hazuki et al., "Bifidobacterium breve A1 supplementation improved Cognitive Decline in Older Adults with Mild Cognitive Impairment: an open label, single arm study," Proceedings of the Annual Meeting of Japan Society for Bioscience, Biotechnology, and Agrochemistry, 2018, #3B07a07.

Kobayashi, Y. et al., "Effects of Bifidobacterium breve A1 on the cognitive function of older adults with memory complaints: a randomised, double-blind, placebo-controlled trial," Beneficial Microbes, May 2019, vol. 10, No. 5, pp. 511-520.

Kobayashi, Y. et al., "Therapeutic potential of Bifidobacterium breve strain A1 for preventing cognitive impairment in Alzheimer's disease," Scientific Reports, 7-13510,2017.

Xiao, J. Z. et al., "Probiotic Bifidobacterium breve in Improving Cognitive Functions of Older Adults with Suspected Mild Cognitive Impairment: A Randomized, Double-Blind, Placebo-Controlled Trial," Journal of Alzheimer's Disease, Sep. 2020, vol. 77, No. 1, pp. 139-147.

Talani, G. et al., "Treatment with gut bifidobacteria improves hippocampal plasticity and cognitive behavior in adult healthy rats," Neuropharmacology, Dec. 2019 Epub, vol. 165, #107909.

Bernier, F, et al., "Association of Plasma Hemoglobin A1c with Improvement of Cognitive Functions by Probiotic Bifidobacterium breve Supplementation in Healthy Adults with Mild Cognitive Impairment," J. Alzheimer's Dis. 2021;81:493-497.

Ishii, T., et al., "Oral Administration of Probiotic Bifidobacterium breve Improves Facilitation of Hippocampal Memory Extinction via Restoration of Aberrant Higher Induction of Neuropsin in an MPTP-Induced Mouse Model of Parkinson's Disease," Biomed. 2021;9:167, 14 pp.

International Search Report for PCT Patent App. No. PCT/JP2021/016150 (Jun. 8, 2021).

Yao, R. et. al., "Bifidobacterium breve MCC1274 with glycosidic activity enhances in vivo isoflavone bioavailability, Beneficial Microbes," May 2019, vol. 10, No. 5, pp. 521-531.

Search Report issued by the China National Intellectual Property Administration on May 17, 2023, with translation.

Notice of Allowance issued by the Korean Intellectual Property Office for Korean Patent Application No. 10-2022-7043966 on Sep. 20, 2023, with translation.

Chinese Office Action (Decision of Rejection) for Chinese Patent Application No. 202310052444.9 (dated Jan. 6, 2024) with English language translation thereof.

Deming Peng et al., Laonian Chidai Fangzhi (Alzheimer's prevention and treatment), Henan Science and Technology Press, Nov. 30, 2018.

Savignac, H. M., et al., "Bifidobacteria modulate cognitive processes in an anxious mouse strain," Behavioural Brain Res. 2015;287:59-72.

Wall, R., et al., "Contrasting effects of Bifidobacterium breve NCIMB 702258 and Bifidobacterium breve DPC 6330 on the composition of murine brain fatty acids and gut microbiota," Am. J. Clin. Nutr. 2012;95:1278-1287.

Yurko-Mauro, K., et al., "Beneficial effects of docosahexaenoic acid on cognition in age-related cognitive decline," Alzheimer's & Dementia 2010;6:456-464.

Kontani, M., et al., "Improvement Effects of a New Supplement Containing Arachidonic Acid (ARA) and Docosahexaenoic acid (DHA) for Dementia Symptoms in Aged Dogs," Japanese Journal of Small Animal Practice 2007;26(5):315-320.

Bhattacharjee, S., et al., "Alzheimer's disease and the microbiome," Frontiers in Cellular Neuroscience 2013; 7:pp. 1-4; Article 153.

Database GNPD [Online] MINTEL: Jan. 29, 2016, anonymous: "Honey Flavoured Stage 3 Milk Powder," XP055643660, retrieved from www.gnpd.com, database accession No. 3751467, pp. 1-4.

Supplementary European Search Report for European Patent App. No. 17806709.6 (Dec. 6, 2019).

Non-Final Office Action for U.S. Appl. No. 16/202,274 dated Aug. 7, 2020.

Tomosada, Y., et al., "Immunoregulatory Effect of Bifidobacteria Strains in Porcine Intestinal Epithelial Cells through modulation Ubiquitin-Editing Enzyme A20 Expression," PLOS ONE 2013;8(3):e59259: pp. 1-12.

Notice of Allowance for U.S. Appl. No. 16/202,274 dated Dec. 24, 2020.

Decision of Refusal for Japanese Patent App. No. 2021-173451 (Mar. 3, 2026) with English language machine translation thereof.

Oshikubo, G., et al., "Utility of VSRAD for diagnosing Alzheimer's disease in patients screened for dementia," J. Int. Med. Res. 2020;48(4):1-10.

Tokuchi, R., et al., "Clinical and demographic predictors of mild cognitive impairment for converting to Alzheimer's disease and reverting to normal cognition," J. Neurological Sciences 2014;346(1-2):288-292.

Shimizu, S., "Relations between VSRAD-based Parahippocampal Atrophy and Results of Neuropsychological Tests in Patients with Alzheimer's Disease and in Those with Mild Cognitive Impairment," J. Kanazawa Med. Univ. 2008;33:145-152, with English language abstract.

* cited by examiner

PROPHYLACTIC AGENT FOR BRAIN ATROPHY, METHOD FOR PREVENTING BRAIN ATROPHY, CULTURE, USE OF CULTURE, FOOD OR BEVERAGE, FOOD FOR PREVENTING BRAIN ATROPHY, SUPPLEMENT FOR PREVENTING BRAIN ATROPHY AND MEDICINE FOR PREVENTING BRAIN ATROPHY

This application claims priority under 35 U.S.C. § 371 to International Application No. PCT/JP2022/039307, filed Oct. 21, 2022, and claims priority therethrough under 35 U.S.C. § 119 to Japanese Patent Application No. 2021-173451, filed Oct. 22, 2021, the entireties of which, as well as all citations cited herein, are incorporated by reference herein.

TECHNICAL FIELD

This disclosure relates to a brain atrophy suppressor, a method for suppressing brain atrophy, a culture, use of a culture, a food or a drink, a supplement for suppressing brain atrophy and a medicine for suppressing brain atrophy.

The present application claims priority from patent application No. 2021-173451 filed in Japan on Oct. 22, 2021, and the contents thereof are incorporated here by reference.

BACKGROUND ART

Brain functions of humans, such as learning ability and memory, gradually decline with age, and forgetfulness, anxiety disorder, decrease in motivation, decrease in sleep quality and the like are apt to be caused. In addition to the laws of nature, when a person is afflicted with dementia, a serious situation which may even threaten human dignity may be caused. At the moment, prevention and treatment of dementia are energetically studied.

PTL 1 discloses a brain function-improving agent for preventing, treating and/or improving one or more declined brain functions selected from the group consisting of dementia, depression, schizophrenia, delirium, amnesia, reduced cognitive ability and intelligent dysfunction containing *Bifidobacterium breve* MCC1274 (FERM BP-11175) and/or a culture containing *Bifidobacterium breve* MCC1274 (FERM BP-11175) as an active ingredient.

CITATION LIST

Patent Literature

PTL 1: JP6853821B

SUMMARY OF INVENTION

Technical Problem

Dementia refers to a condition in which the patient continuously has problems in the life due to the inability to make decisions and rapid decline in memory and which is caused by various disorders caused by brain cell death due to various causes or deterioration of the functions. The most common factor for developing dementia is neurodegenerative diseases, in which neurons in the brain gradually die, and the next common factor is cerebrovascular dementia. The neurodegenerative diseases include Alzheimer's disease, frontotemporal dementia, Lewy body dementia and the like. Cerebrovascular dementia is caused by death of neurons in the brain or damage to the neural networks triggered by cerebral infarction, brain hemorrhage, cerebral arteriosclerosis or the like.

Alzheimer's disease is a neurodegenerative disease which accounts for 50% to 60% of dementia cases. The neuropathological characteristics of Alzheimer's disease are neurofibrillary degeneration in the cerebral cortex and the hippocampus, senile plaque and enormous neuron exfoliation. In neurofibrillary degeneration, a tau protein, which is a microtubule-associated protein, is excessively phosphorylated to form a fiber inclusion body. Senile plaque is extracellular accumulation of amyloid β-protein. In Alzheimer's disease, the accumulation of amyloid β-protein accelerates neurofibrillary degeneration, and the fibrotic tau protein inhibits intracellular transport. Furthermore, amyloid β-protein itself is cytotoxic, such as impairment of synapse functions.

With the coming of a super-aged society, the number of dementia patients will increase rapidly, which causes a concern about social issues. Accordingly, studies are currently required on prevention of the onset of dementia such as Alzheimer's disease, improvement thereof and suppression of progress thereof especially through intervention in daily life habits such as diet.

One of four older adults is said to suffer from mild cognitive impairment (also called MCI) or dementia. MCI is a condition that precedes dementia. MCI does not interrupt daily living unlike dementia, but MCI is said to associate with a decline of ability such as memory and be at the boundary between healthy individuals and dementia. It is said that about a half of those diagnosed with MCI will develop Alzheimer-type dementia within five years.

An object of this disclosure is to provide a brain atrophy suppressor, a method for suppressing brain atrophy, a culture or use of a culture which can suppress the progress of brain atrophy in a subject selected from a healthy individual, an individual diagnosed with mild cognitive impairment, an individual assessed as having cognitive decline and a subject at a risk of a neurodegenerative disease.

Solution to Problem

In an aspect of this disclosure, a brain atrophy suppressor containing a culture containing *Bifidobacterium breve* MCC1274 (FERM BP-11175) as an active ingredient which is administered to a subject selected from a healthy individual, an individual diagnosed with mild cognitive impairment, an individual assessed as having cognitive decline and a subject at a risk of a neurodegenerative disease is provided.

In another aspect of this disclosure, a method for suppressing brain atrophy including administering a culture containing *Bifidobacterium breve* MCC1274 (FERM BP-11175) in an effective amount for suppressing brain atrophy to a subject selected from a healthy individual in need of suppression of brain atrophy, an individual diagnosed with mild cognitive impairment, an individual assessed as having cognitive decline and a subject at a risk of a neurodegenerative disease is provided.

In another aspect of this disclosure, a culture containing *Bifidobacterium breve* MCC1274 (FERM BP-11175) for use in the suppression of brain atrophy of a subject selected from a healthy individual, an individual diagnosed with mild cognitive impairment, an individual assessed as having cognitive decline and a subject at a risk of a neurodegenerative disease is provided.

In another aspect of this disclosure, use of a culture containing *Bifidobacterium breve* MCC1274 (FERM BP-11175) for the manufacture of a brain atrophy suppressor which is administered to a subject selected from a healthy individual, an individual diagnosed with mild cognitive impairment, an individual assessed as having cognitive decline and a subject at a risk of a neurodegenerative disease is provided.

Advantageous Effects of Invention

According to this disclosure, a brain atrophy suppressor, a method for suppressing brain atrophy, a culture or use of a culture which can suppress the progress of brain atrophy in a subject selected from a healthy individual, an individual diagnosed with mild cognitive impairment, an individual assessed as having cognitive decline and a subject at a risk of a neurodegenerative disease is provided.

The effect described here is not necessarily limited and may also be any of the effects described in the present specification.

DESCRIPTION OF EMBODIMENTS

Figure 1:
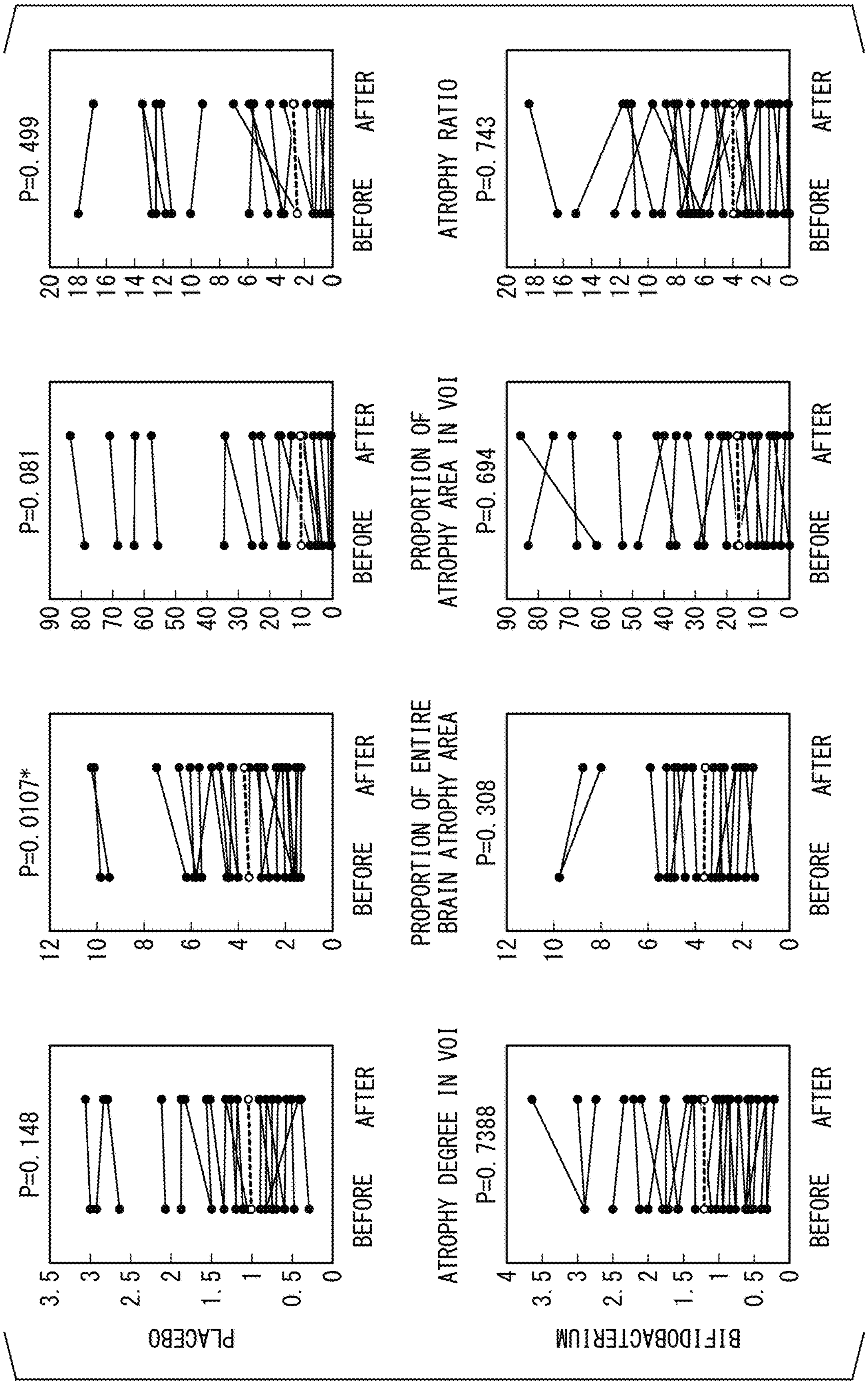
FIG. 1 is a graph showing the changes in the VSRAD scores of the subjects (A: *Bifidobacterium* intake group, B: placebo intake group).

Although embodiments according to this disclosure will be explained in detail below, this disclosure is not limited to the embodiments described below, and various modifications are possible as long as the modifications do not depart from the gist of this disclosure.

The "brain atrophy" according to this disclosure refers to atrophy in the brain that is characteristically observed or physiological brain atrophy observed with aging.

The "suppression" in this disclosure means prevention or delay of progress to a worse state, and the "suppression of brain atrophy" refers to suppression of atrophy in the brain which progresses with the neurodegenerative diseases above or physiological brain atrophy observed with aging.

The "improvement" in this disclosure means improvement of a symptom or a disease, prevention or delay of deterioration of a symptom or a disease, reversal, prevention or delay of progress of a symptom or a disease, treatment of a symptom or a disease or the like. The "improvement" in this disclosure also includes the meanings of prevention.

The "prevention" in this disclosure means prevention of the onset or delay of the onset of a symptom or a disease in the subject of the application, reduction of the risk of the onset of a symptom or a disease of the subject of the application or the like.

The composition of the present invention can suppress brain atrophy caused by exfoliation of neurons and can improve a decline of cognitive functions caused by the brain atrophy in the neurodegenerative diseases above. Moreover, the composition of the invention can also suppress physiological brain atrophy which appears or progresses with aging and can improve a decline of cognitive functions caused by the physiological brain atrophy, such as a decline of memory, poor concentration and decreased thinking ability which are observed in a healthy individual with aging.

The inventors of the present application have found that atrophy in brain areas including the hippocampus, the parahippocampal gyrus and the tonsils is suppressed and that cognitive functions such as orientation are improved when an individual diagnosed with MCI takes a culture containing *Bifidobacterium breve* MCC1274 (FERM BP-11175), compared to a case without the intake.

<Brain Atrophy Suppressor, Culture and Use of Culture>

The brain atrophy suppressor of this disclosure is a brain atrophy suppressor containing a culture containing *Bifidobacterium breve* MCC1274 (FERM BP-11175) as an active ingredient which is administered to a subject diagnosed with mild cognitive impairment.

The active ingredient of the brain atrophy suppressor of this disclosure is a culture of *Bifidobacterium breve*, which lives in abundance mainly in the large intestines of infants and small children. Accordingly, the brain atrophy suppressor of this disclosure is highly safe, is not likely to cause need for worries for side effects even after long-term continuous administration and is very useful. Furthermore, the brain atrophy suppressor of this disclosure is highly safe even in a combination use with another drug.

In this disclosure, the subject of the administration of the brain atrophy suppressor may be any subject as long as the subject is a healthy individual but is desirably an individual determined to have mild cognitive impairment. Moreover, the subject of the administration of the brain atrophy suppressor is suitably an older adult, a middle-aged adult or an adult in the prime of life who is a healthy individual requiring prevention of a decline of cognitive functions, such as an individual having a symptom or a disorder due to cognitive decline and an older adult, a middle-aged adult or an adult in the prime of life at a risk of cognitive decline, or the like.

Furthermore, the method of this disclosure is suitably applied to a patient of a neurodegenerative disease which is known to show brain atrophy, such as Alzheimer-type dementia, an older adult, a middle-aged adult or an adult in the prime of life at a risk of the neurodegenerative disease, an older adult at a risk of brain atrophy and the like.

The healthy individual in this disclosure means an individual who does not have any specific chronic diseases and who does not have any problem in activities in the daily life.

In this disclosure, MCI means an individual whose main symptom is forgetfulness but who is in a state which cannot be diagnosed with dementia because the daily life is rarely affected.

Mild cognitive impairment is a stage before dementia and is believed to be a stage between healthy individuals and dementia patients, and mild cognitive impairment refers to a state which is not diagnosed with dementia although the cognitive functions are declined more than expected for the normal aging process.

As definitions of mild cognitive impairment, the following three are included.

1. The individual or family member complains of a decline of cognitive functions (memory, decision making, reasoning and ability to act).
2. Although the cognitive functions are not normal, the diagnostic criteria of dementia are not satisfied.
3. The individual has minimal disability in complex daily activities but can lead a normal daily life.

Furthermore, MCI also includes, as an example, an individual diagnosed with MCI by the diagnostic criteria of dementia (major neurocognitive disorder) according to the Diagnostic and Statistical Manual of Mental Disorders, Fifth Edition (DSM-5) of the American Psychiatric Association.

The diagnostic criteria (2013) of dementia according to DSM-5 are as follows.

A. The evidence of significant cognitive decline from a previous level of performance in one or more cognitive domains (complex attention, executive function, learning and memory, language, perceptual-motor and social cognition) is based on:

(1) concern of the individual, a knowledgeable informant or the clinician that there has been a significant decline in cognitive function; and (2) a substantial impairment in cognitive performance documented by standardized neuropsychological testing or, in its absence, another quantified clinical assessment.

B. The cognitive deficits interfere with independence in everyday activities (namely, at a minimum, requiring assistance with complex instrumental activities of daily living such as paying bills and managing medications).

C. The cognitive deficits do not occur exclusively in the context of a delirium.

D. The cognitive deficits are not better explained by another mental disorder (example: depression and schizophrenia).

Further preferably, an individual determined to have MCI who satisfies one or more of the inclusion criteria below, preferably all, and who does not fall in any of the exclusion criteria below is preferable.

(Inclusion Criteria)

(1) A male or a female aged 65 years or older and younger than 90 years old at the point of consent.

(2) An individual who is diagnosed with MCI by DSM-5 (the Diagnostic and Statistical Manual of Mental Disorders, Fifth Edition, 2013, the American Psychiatric Association) and who satisfies the objective evidences in a) to c) below.

a) The individual or family member complains of memory impairment.

b) The Mini Mental State Examination (MMSE) score is 22 or more and 26 or less.

c) The Clinical Dementia Rating (CDR is 0.5 (suspected dementia).

(3) Informed consent to participate in the trial is obtained in writing.

(Exclusion Criteria)

Parkinson's disease, Huntington's disease, normal pressure hydrocephalus, progressive supranuclear palsy, epilepsy, multiple sclerosis, intracranial infection or head trauma with aftereffect.

History of major depression, bipolar disorder or addiction to alcohol or another substance. Findings of multiple cerebral infarction, brain tumor or subdural hematoma.

Cognitive dysfunction due to lack of vitamin B12 or folic acid.

Neurosyphilis.

Cognitive dysfunction due to thyroid dysfunction.

An individual with a severe cerebrovascular disease, a heart disease, a liver disease, a renal disease, a gastrointestinal disease, an endocrine and metabolic disorder, a notifiable infectious disease or the like.

An individual with history of digestive system cancer or an individual currently receiving therapy or medication due to the disease.

An individual with history of major operation in the digestive system, such as gastrectomy, gastrointestinal tract suturing or intestinal resection. An individual having gastrointestinal dysfunction such as inflammatory bowel disease.

Regular user of a pharmaceutical product (antibiotics, intestinal regulators, laxatives and antidiarrheics) or a health food or a supplement (lactic acid bacteria, bifidobacteria, oligosaccharides, dietary fiber and the like) which affects the bowel movement.

An individual with remarkable abnormality found in blood pressure measurement or blood testing.

An individual with severe anemia.

An individual who may have allergic reaction to a drug or food.

Heavy smoker, habitual user of excessive alcohol and an individual with excessively irregular lifestyle for a meal, sleep or the like.

User of an anti-dementia drug or a psychoactive drug (antidepressants, antipsychotic drugs and the like). Severe diabetes with insulin administration.

User of a pacemaker, an aneurysm clip, a prosthetic valve, a cochlear implant or another magnetic or conductive metal which causes a problem in brain MRI imaging.

A participant or a planned participant of a clinical trial of a new therapeutic drug for Alzheimer-type dementia who may participate both in the trial and this trial. An individual who participates in another clinical trial or who has participated within one month.

An individual considered by the principal investigator to be ineligible.

In this disclosure, for brain atrophy, images are analyzed using MRI examination data, and the volume of the cerebral cortex is compared with that of a healthy individual.

For example, assessment is made by analyzing MRI (Magnetic Resonance Imaging) images using VSRAD (registered trademark, Voxel-based Specific Regional analysis system for Alzheimer's Disease) (manufactured by Eisai Co., Ltd., https://medical.eisai.jp/products/vsrad/) or image analysis software "Pmod3.7" (Pmod Technologies Ltd.).

VSRAD is diagnosis support software to assess the degree of progress of Alzheimer-type dementia using MRI examination data and can assess the atrophy degree of the parahippocampal gyrus, the hippocampus and the tonsils. The parahippocampal gyrus, the hippocampus and the tonsils are sometimes called VOI (Volume Of Interest).

The atrophy in the VOI area is represented by a numerical value called "VOI atrophy degree". (See Hiroshi Matsuda, "III. Learning Image Statistic Software—Acquisition Method, Characteristics, Utility, Problems, 1. Including VSRAD-DARTEL", monthly INNERVISION, INNERVISION Co., Ltd., Dec. 25, 2010, Vol. 26., No. 1, p 29-32)

1) Atrophy degree of 0 to 1: Low possibility of Alzheimer-type dementia.

2) Atrophy degree of 1 to 2: When mild atrophy is observed, further follow-up observation and continued MRI examination are required.

3) Atrophy degree of 2 to 3: When strong atrophy is observed, the possibility of having Alzheimer-type dementia is higher.

4) Atrophy degree of 3 or more: The patient is almost certain to have dementia and will require treatment for dementia.

In this regard, however, definitive diagnosis of dementia is not possible based solely on VSRAD.

In this disclosure, suppression of brain atrophy is determined by the following criteria. It is determined that brain atrophy is suppressed when a brain atrophy suppressor etc. intake group has a statistical significance compared to a placebo group, as a result of comparison between the measured values at the start of examination (also called week 0) and the measured values 24 weeks after starting examination with respect to at least one of the VSRAD scores (the Z score in the VOI, the proportion of the entire brain atrophy area, the proportion of the atrophy area in the VOI and the atrophy ratio (inside VOI/entire brain)) which are obtained by analyzing head MRI images by VSRAD, for the placebo group and the brain atrophy suppressor etc. intake group. For example, when the measured value of at least one of the VSRAD scores 24 weeks after starting examination is significantly decreased from the measured value at the start of examination in the placebo group while there is no significant decrease in the measured value of the score 24 weeks after starting examination from the measured value at the start of examination in the brain atrophy suppressor etc. intake group, it is determined that brain atrophy is suppressed. In this disclosure, the brain atrophy suppressor etc. intake group means a group with intake of at least one of a brain atrophy suppressor food or drink, a food for suppressing brain atrophy, a supplement for suppressing brain atrophy and a medicine for suppressing brain atrophy.

In this disclosure, for cognitive functions, the change thereof is assessed using ADAS-Jcog. (Alzheimer's Disease Assessment Scale-cognitive component-Japanese version).

In ADAS-Jcog., cognitive functions are assessed by 11 items of word recall, spoken language ability, acoustic comprehension of language, word-finding difficulty in spontaneous talk, following oral commands, naming fingers and objects, constructional praxis, ideational praxis, orientation, word recognition and ability of remembering test instructions, and the score range is 0 to 70. A higher score means poorer cognitive functions, because 0 point is given when all the answers are correct, and 70 points are given when all the answers are incorrect. ADAS-Jcog. is often used as a standard testing method in clinical trials of Alzheimer's disease.

In this disclosure, cognitive decline refers to a state in which the MMSE score is 22 or more and 26 or less and in which CDR is 0.5.

In this disclosure, improvement of cognitive functions is determined by the following criteria. It is determined that cognitive functions are improved when a brain atrophy suppressor etc. intake group has a statistical significance compared to a placebo group, as a result of comparison between the scores at the start of examination (also called week 0) and the scores 24 weeks after starting examination with respect to at least one item of word recall, spoken language ability, acoustic comprehension of language, word-finding difficulty in spontaneous talk, following oral commands, naming fingers and objects, constructional praxis, ideational praxis, orientation, word recognition and ability of remembering test instructions, for the placebo group and the brain atrophy suppressor etc. intake group. For example, when the measured value of at least one of the scores 24 weeks after starting examination is significantly increased from the measured value at the start of examination in the placebo group while the measured value of the score 24 weeks after starting examination is slightly increased or decreased from the measured value at the start of examination in the brain atrophy suppressor etc. intake group, it is determined that cognitive functions are improved. In particular, in this disclosure, when the score of orientation of the brain atrophy suppressor etc. intake group has a statistical significance as a result of comparison between the placebo group and the brain atrophy suppressor etc. intake group, it can be determined that cognitive functions are improved. The statistical significance means $p$ value<0.05.

*Bifidobacterium breve* is a bacterial species belonging to the *Bifidobacterium. Bifidobacterium breve* lives in abundance mainly in the large intestines of infants and small children. *Bifidobacterium breve* is known as an infant- and small children-type *Bifidobacterium* species together with *Bifidobacterium longum* subsp. *infantis* and the like of the bacterial species belonging to the *Bifidobacterium.*

*Bifidobacterium breve* in this disclosure especially refers to the specific bacterial strain given a number MCC1274 (FERM BP-11175). MCC1274 has been deposited to International Patent Organism Depositary, National Institute of Advanced Industrial Science and Technology (Center 6, 1-1-1 Higashi, Tsukuba-shi, Ibaraki 305-8566, Japan (Current IPOD, International Patent Organism Depositary, National Institute of Technology and Evaluation (NITE-IPOD): #120, 2-5-8 Kazusakamatari, Kisarazu-shi, Chiba 292-0818, Japan))) since Aug. 25, 2009 with an accession number IPOD FERM BP-11175.

A culture containing *Bifidobacterium breve* MCC1274 (FERM BP-11175) can be easily obtained, for example, by culturing *Bifidobacterium breve* MCC1274 (FERM BP-11175). The culture method is not particularly limited as long as the bacterium can grow, and the bacterium can be cultured under appropriate conditions. Specifically, for example, the culture temperature is generally 25 to 50° C. and is preferably 35 to 42° C. The bacterium is preferably cultured under an anaerobic condition and can be cultured, for example, while sending an anaerobic gas such as carbon dioxide gas. Furthermore, the bacterium may be cultured under a microaerophilic condition such as static liquid culture.

The medium for culturing *Bifidobacterium breve* MCC1274 (FERM BP-11175) used in this disclosure is not particularly limited, and a medium which is generally used for culturing a bacterium belonging to the *Bifidobacterium* can be used.

That is, as a carbon source, for example, saccharides such as glucose, galactose, lactose, arabinose, mannose, sucrose, starch, starch hydrolysate and molasses can be used depending on the assimilation properties. As a nitrogen source, for example, ammonia and ammonium salts and nitrates such as ammonium sulfate, ammonium chloride and ammonium nitrate can be used. Moreover, as an inorganic salt, for example, sodium chloride, potassium chloride, potassium phosphate, magnesium sulfate, calcium chloride, calcium nitrate, manganese chloride, ferrous sulfate and the like can be used. Furthermore, organic components such as peptone, soybean powder, a defatted soybean cake, meat extract and yeast extract may also be used.

As *Bifidobacterium breve* MCC1274 (FERM BP-11175) used in this disclosure, the obtained culture may be used directly after culture or used after dilution or concentration, or bacterial cells collected from the culture may also be used. The "culture" in this disclosure is a concept which also contains a culture supernatant.

The culture containing *Bifidobacterium breve* MCC1274 (FERM BP-11175) which the brain atrophy suppressor of this disclosure contains as an active ingredient may be of one kind or of two or more kinds. Moreover, the brain atrophy suppressor of this disclosure may be composed only of the active ingredient or may be a composition containing the active ingredient and any component other than the active ingredient. The component is not particularly limited, and an additive which has been conventionally blended in medicines (for example, the carrier for formulation described below and the like) can be blended.

The culture containing *Bifidobacterium breve* MCC1274 (FERM BP-11175) can be subjected to use in the suppression of brain atrophy of a healthy individual, an individual diagnosed with mild cognitive impairment, an individual assessed as having cognitive decline and a subject at a risk of a neurodegenerative disease.

The culture containing *Bifidobacterium breve* MCC1274 (FERM BP-11175) for use in the suppression of brain atrophy of this disclosure is preferably orally administered to a healthy individual, an individual diagnosed with mild cognitive impairment and a subject at a risk of cognitive decline and a neurodegenerative disease in such a manner that the *Bifidobacterium breve* MCC1274 (FERM BP-11175) is at $1.0\times10^{6}$ to $1.0\times10^{12}$ CFU per day, more preferably orally administered at $1.0\times10^{8}$ to $1.0\times10^{12}$ CFU and further preferably orally administered at $1.0\times10^{9}$ to $1.0\times10^{11}$ CFU.

Here, the CFU indicates colony forming unit.

The culture containing *Bifidobacterium breve* MCC1274 (FERM BP-11175) can be subjected to use for the manufacture of a brain atrophy suppressor to be administered to a healthy individual, an individual diagnosed with mild cognitive impairment, an individual assessed as having cognitive decline and a subject at a risk of a neurodegenerative disease.

The brain atrophy suppressor containing a culture containing *Bifidobacterium breve* MCC1274 (FERM BP-11175) as an active ingredient of this disclosure is preferably orally administered to a healthy individual, an individual diagnosed with mild cognitive impairment, an individual assessed as having cognitive decline and a subject at a risk of at least one of neurodegenerative diseases in such a manner that the *Bifidobacterium breve* MCC1274 (FERM BP-11175) is at $1.0\times10^{6}$ to $1.0\times10^{12}$ CFU per day, more preferably orally administered at $1.0\times10^{8}$ to $1.0\times10^{12}$ CFU and further preferably orally administered at $1.0\times10^{9}$ to $1.0\times10^{11}$ CFU.

<Suppression Method for Brain Atrophy>

The method for suppressing brain atrophy of this disclosure includes orally administering $1.0\times10^{6}$ to $1.0\times10^{12}$ CFU per day of a culture containing *Bifidobacterium breve* MCC1274 (FERM BP-11175) in an effective amount for suppressing brain atrophy to a healthy individual in need of suppression of brain atrophy, an individual diagnosed with mild cognitive impairment, an individual assessed as having cognitive decline and a subject at a risk of a neurodegenerative disease. The effective amount for suppressing brain atrophy is preferably $1.0\times10^{8}$ to $1.0\times10^{12}$ CFU per day, more preferably $1.0\times10^{9}$ to $1.0\times10^{11}$ CFU. Here, the effective amount for suppressing brain atrophy is the *Bifidobacterium breve* MCC1274 (FERM BP-11175) content.

Through suppression of brain atrophy, Alzheimer's disease, frontotemporal dementia, Lewy body disease, cerebral infarction and a cerebrovascular disease such as brain hemorrhage can be prevented. The composition for suppressing brain atrophy of the invention is effective also on a healthy subject in particular as preclinical measure or from a prophylactic point.

<Medicine>

In this disclosure, a medicine for suppressing brain atrophy containing a culture containing *Bifidobacterium breve* MCC1274 (FERM BP-11175) as an active ingredient for administration to a healthy individual, an individual diagnosed with mild cognitive impairment, an individual assessed as having cognitive decline and a subject at a risk of at least one of neurodegenerative diseases is also provided.

The medicine of this disclosure can be appropriately formulated into a desired dosage form suitable for oral administration. The dosage form is not particularly limited, but for example, the medicine can be formulated into a solid preparation such as powder, granules, tablets, troches and capsules, a liquid preparation such as a solution, a syrup, a suspension and an emulsion or the like. The formulation can be appropriately conducted by a known method depending on the dosage form.

For formulation, the medicine of this disclosure may be formulated, for example, by appropriately blending a carrier for formulation. Moreover, in addition to the culture containing *Bifidobacterium breve* MCC1274 (FERM BP-11175), a component which is generally used for formulation, such as excipients, pH-adjusting agents, colorants and corrigents, can be used. A component having the effect of preventing, treating and/or improving a disease or a symptom which is known or will be found in the future can also be appropriately used in combination depending on the purpose.

As the carrier for formulation, an organic or inorganic carrier can be used depending on the dosage form. Examples of the carrier for a solid preparation include excipients, binders, disintegrating agents, lubricants, stabilizers, flavoring agents and the like.

Examples of the excipients include: saccharide derivatives such as lactose, sucrose, glucose, mannitol and sorbitol; starch derivatives such as cornstarch, potato starch, α-starch, dextrin and carboxymethyl starch; cellulose derivatives such as crystalline cellulose, hydroxypropyl cellulose, hydroxypropyl methylcellulose, carboxymethylcellulose and carboxymethyl cellulose calcium; gum arabic; dextran; pullulan; silicate derivatives such as light silicic anhydride, synthetic aluminum silicate and magnesium aluminometasilicate; phosphate derivatives such as calcium phosphate; carbonate derivatives such as calcium carbonate; sulfate derivatives such as calcium sulfate; and the like.

Examples of the binders include, in addition to the excipients, gelatin, polyvinylpyrrolidone, macrogol and the like.

Examples of the disintegrating agents include, in addition to the excipients, chemically modified starch or cellulose derivatives such as croscarmellose sodium, sodium carboxymethyl starch and cross-linked polyvinylpyrrolidone and the like.

Examples of the lubricants include: talc; stearic acid; metal stearates such as calcium stearate and magnesium stearate; colloidal silica; waxes such as Veegum and spermaceti wax; boric acid; glycols; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acid such as silicic anhydride and silicic acid hydrate; starch derivatives; and the like.

Examples of the stabilizers include: paraoxybenzoate esters such as methylparaben and propylparaben; alcohols such as chlorobutanol, benzyl alcohol and phenylethyl alcohol; benzalkonium chloride; acetic anhydride; sorbic acid; and the like.

Examples of the flavoring agents include sweeteners, acidulants, aromas and the like.

In this regard, the carrier used in the case of a liquid preparation for oral administration is a solvent such as water, a flavoring agent or the like.

The amount of the culture containing *Bifidobacterium breve* MCC1274 (FERM BP-11175) contained in the medicine of this disclosure is not particularly restricted, but the medicine preferably contains the culture containing *Bifidobacterium breve* MCC1274 (FERM BP-11175) in an amount which allows reasonable intake of a daily dose for an effective brain atrophy-suppressing effect, more preferably contains $1.0\times10^{6}$ to $1.0\times10^{12}$ CFU/g of *Bifidobacterium*

*breve* MCC1274 (FERM BP-11175), further preferably contains $1.0\times10^{8}$ to $1.0\times10^{12}$ CFU/g and particularly preferably contains $1.0\times10^{9}$ to $1.0\times10^{11}$ CFU/g. The daily dose of the culture containing *Bifidobacterium breve* MCC1274 (FERM BP-11175) in the medicine of this disclosure is in such a manner that at least *Bifidobacterium breve* MCC1274 (FERM BP-11175) is preferably at $1.0\times10^{6}$ CFU/g or more, more preferably at $1.0\times10^{6}$ to $1.0\times10^{12}$ CFU/g, further preferably at $1.0\times10^{8}$ to $1.0\times10^{12}$ CFU/g, particularly preferably at $1.0\times10^{9}$ to $1.0\times10^{11}$ CFU/g.

The daily dose of the medicine of this disclosure may be orally administered once a day to in three divided portions per day. The subject of administration is generally human, but in this disclosure, the subject also includes a mammal other than human, such as pet animals including dog, cat and the like and livestock including cow, sheep, pig and the like.

<Food or Drink, Food and Supplement>

In this disclosure, a food or a drink containing a culture containing *Bifidobacterium breve* FERM BP-11175 which is labeled with a brain atrophy-suppressing effect on a healthy individual, an individual diagnosed with mild cognitive impairment, an individual assessed as having cognitive decline and a subject at a risk of a neurodegenerative disease and a supplement containing a culture containing *Bifidobacterium breve* FERM BP-11175 as an active ingredient which is taken by a subject diagnosed with mild cognitive impairment are also provided.

The food or the drink and the food are not limited regarding the form such as liquid, paste, solid and powder, and examples thereof include, in addition to tablet candies, liquid foods, feed (including food for pets) and the like, wheat products, instant foods, processed agricultural products, processed fishery products, processed livestock products, milk/dairy products, oils and fats, basic condiments, compound flavor enhancers/foods, frozen foods, confectioneries, drinks, other commercial foods and the like.

Examples of the dairy products include fermented milk, milk beverages, lactic acid bacteria beverages, sweetened condensed milk, skim milk powder, sweetened milk powder, powdered formula, creams, cheeses, butter, ice creams and the like.

Examples of the wheat products include breads, macaroni, spaghetti, noodles, cake mixes, frying flours, bread crumbs and the like.

Examples of the instant foods include instant noodles, cup noodles, retort-pouched/prepared foods, prepared canned foods, microwave foods, instant soups/stews, instant miso soups/clear Japanese soups, canned soups, freeze-dried foods, other instant foods and the like.

Examples of the processed agricultural products include canned agricultural products, canned fruits, jams/marmalades, pickles, cooked beans, dried agricultural products, cereals (processed grains) and the like.

Examples of the processed fishery products include canned fishery products, fish hams/sausages, fishery paste products, fishery delicacies, Tsukudani (foods boiled down in sweetened soy sauce) and the like.

Examples of the processed livestock products include canned livestock products/pastes, livestock hams/sausages and the like.

Examples of the oils and fats include butter, margarine, vegetable oils and the like.

Examples of the basic condiments include soy sauce, soybean paste, sauces, processed tomato condiments, Mirin (sweet sake for seasoning), vinegars and the like, and the compound flavor enhancers/foods include cooking mixes, curry roux, sauces, dressings, noodle broths, spices, other compound flavor enhancers and the like.

Examples of the frozen foods include frozen food materials, semi-cooked frozen foods, cooked frozen foods and the like.

Examples of the confectioneries include caramels, candies, chewing gums, chocolates, cookies, biscuits, cakes, pies, snacks, crackers, Japanese-style confectioneries, rice confectioneries, bean confectioneries, desserts, other confectioneries and the like.

Examples of the drinks include carbonated drinks, natural juices, fruit juices, fruit juice-containing soft drinks, fruit flesh drinks, fruit granule-containing fruit juices, vegetable drinks, soy milk, soy milk drinks, coffee drinks, tea drinks, drink powders, concentrated drinks, sport drinks, nutritional drinks, alcohols, other luxury beverages and the like.

Examples of the other commercial foods include baby foods, Furikake (dry Japanese seasonings), seasonings for Chazuke (boiled rice with hot tea) and the like.

Of these, the food or the drink and the food of this disclosure are particularly preferably a dairy product, particularly preferably fermented milk. As a result, in addition to the brain atrophy-suppressing effect, the high nutritional value of a dairy product can also be enjoyed.

Moreover, the supplement of this disclosure is not particularly limited.

The food or the drink, the food and the supplement provided by the invention can be used similarly to the method for using the medicine described in <Medicine> above and can also be used in a range which is not for the purpose of brain atrophy suppression. That is, the food or the drink, the food and the supplement according to the invention can be applied to the subject of application of the medicine in such a manner that the amount of the used *Bifidobacterium breve* MCC1274 (FERM BP-11175) in the food or the drink, the food and the supplement is the same amount as that of *Bifidobacterium breve* MCC1274 (FERM BP-11175) contained in the medicine based on the *Bifidobacterium breve* MCC1274 (FERM BP-11175) contained in the food or the drink, the food and the supplement.

In an embodiment, the food or the drink, the food and the supplement according to the invention can be applied to a subject (for example, a human or another mammal) which does not have any "pathological" or "abnormal" symptom, state or disease, namely a subject (for example, a human or another mammal) in a "healthy" or "normal" state, to maintain or enhance the "healthy" or "normal" state. Furthermore, the application can be for "a healthy individual who is concerned about brain atrophy" or "a healthy individual who is concerned about cognitive decline" to maintain or enhance the "healthy" or "normal" state. In this case, whether the culture containing *Bifidobacterium breve* MCC1274 (FERM BP-11175) is a component of pharmaceutical composition or a component of a food composition, the pharmacological effect of the culture itself containing *Bifidobacterium breve* MCC1274 (FERM BP-11175) is basically the same, and thus the application amount and the application method of the food composition can be appropriately adjusted depending on the expected effect based on the culture containing *Bifidobacterium breve* MCC1274 (FERM BP-11175).

The food or the drink, the food and the supplement which are applied to a subject (for example, a human or another mammal) which does not have any "pathological" or "abnormal" symptom, state or disease, namely a subject (for example, a human or another mammal) in a "healthy" or "normal" state to maintain or enhance the "healthy" or "normal" state are sometimes especially called "functional foods".

In this disclosure, the "labeling" act includes all the acts for informing a consumer of the use of brain atrophy suppression, and all the expressions which can remind of/cause to guess the use are the "labeling" acts of this disclosure, regardless of the purposes of labeling, the contents of labeling, the objects to be labeled, the media and the like.

The "label" is preferably with an expression which allows a consumer to directly recognize the use. Specific examples include an act of transferring an article in which the use is described on a product regarding the food or the drink and the food or packaging of a product, delivering such an article, displaying such an article for transfer or delivery or importing such an article, an act of displaying or distributing an advertisement of a product, a price list or a business document with a description of the use thereon or providing information with such contents with a description of the use by an electromagnetic method (the Internet or the like) and another act.

The content of the label is preferably a label approved by the administration or the like (for example, a label approved based on a system provided by the administration and provided in the form based on the approval or the like). It is preferable to label with such a content on packaging, a container, a catalogue, a brochure, an advertisement material in a sales site such as POP (point of purchase advertising), other documents or the like.

The "labels" also include labels with health foods, functional foods, food for the ill, enteral nutrition products, food for special dietary uses, food with health claims, foods for specified health uses, foods with function claims, foods with nutrient function claims, quasi-drugs and the like. In particular, the labels are labels approved by the Consumer Affairs Agency, such as labels approved by the systems for foods for specified health uses, the systems for foods with function claims and similar systems and the like. More specific examples include a label with foods for specified health uses, a label with qualified foods for specified health uses, a label with foods with function claims, a label indicating influence on the structure or the function of a body, a label with reduction of disease risk and the like. Typical examples thereof include labels with food for specified health uses (especially labels with health uses) provided by the Regulations for Enforcement of the Health Promotion Act (Order of the Ministry of Health, Labour and Welfare of Japan, No. 86, Apr. 30, 2003), labels with foods with function claims provided by the Food Labeling Act (Act No. 70 of 2013), similar labels and the like.

The term used for the labeling described above is not limited only to a term such as "for suppressing brain atrophy and for preventing brain atrophy", and it is needless to mention that any other terms which indicate the effect of preventing, improving and/or treating a disease or a symptom related to suppression of brain atrophy are included in the scope of this disclosure. As such a term, for example, a label based on various uses which allows a consumer to recognize the effect of improving brain atrophy, preventing brain atrophy, inhibiting brain atrophy, improving cognitive functions or enhancing, improving and supporting cognitive functions or orientation can also be used.

EXAMPLES

This disclosure will be explained more specifically below referring to Examples. The Examples described below are merely examples of this disclosure, and this disclosure is not limited by the Examples.

Clinical Trial Example

Trial Regarding Suppression of Brain Atrophy and Improvement f Cognitive Functions through Intake of *Bifidobacterium breve* MCC1274 (FERM BP-11175) (Also Simply Called "*Bifidobacterium*" below) in Subjects Diagnosed with MCI Placebo-Controlled, Randomized Comparison Trial (RCT, Randomized Controlled Trial)

<Subjects>

Of outpatients who visited the Juntendo Tokyo Koto Geriatric Medical Center, Juntendo University Hospital and the like, 130 patients who satisfied all the inclusion criteria below and who did not fall in any of the exclusion criteria below were used as the subjects.

(Inclusion Criteria)

(1) A male or a female aged 65 years or older and younger than 90 years old at the point of consent.

(2) An individual who is diagnosed with =MCI by DSM-5 (the Diagnostic and Statistical Manual of Mental Disorders, Fifth Edition, 2013, the American Psychiatric Association) and who satisfies the objective evidences in a) to c) below.

a) The individual or family member complains of memory impairment.

b) The Mini Mental State Examination (MMSE) score is 22 or more and 26 or less.

c) The Clinical Dementia Rating (CDR is 0.5 (suspected dementia).

(3) Informed consent to participate in the trial is obtained in writing.

(Exclusion Criteria)

Parkinson's disease, Huntington's disease, normal pressure hydrocephalus, progressive supranuclear palsy, epilepsy, multiple sclerosis, intracranial infection or head trauma with aftereffect.

History of major depression, bipolar disorder or addiction to alcohol or another substance. Findings of multiple cerebral infarction, brain tumor or subdural hematoma.

Cognitive dysfunction due to lack of vitamin B12 or folic acid.

Neurosyphilis.

Cognitive dysfunction due to thyroid dysfunction.

An individual with a severe cerebrovascular disease, a heart disease, a liver disease, a renal disease, a gastrointestinal disease, an endocrine and metabolic disorder, a notifiable infectious disease or the like.

An individual with history of digestive system cancer or an individual currently receiving therapy or medication due to the disease.

An individual with history of major operation in the digestive system, such as gastrectomy, gastrointestinal tract suturing or intestinal resection. An individual having gastrointestinal dysfunction such as inflammatory bowel disease.

Regular user of a pharmaceutical product (antibiotics, intestinal regulators, laxatives and antidiarrheics) or a health food or a supplement (lactic acid bacteria, bifidobacteria, oligosaccharides, dietary fiber and the like) which affects the bowel movement.

An individual with remarkable abnormality found in blood pressure measurement or blood testing.

An individual with severe anemia.

An individual who may have allergic reaction to a drug or food.

Heavy smoker, habitual user of excessive alcohol and an individual with excessively irregular lifestyle for a meal, sleep or the like.

User of an anti-dementia drug or a psychoactive drug (antidepressants, antipsychotic drugs and the like). Severe diabetes with insulin administration.

User of a pacemaker, an aneurysm clip, a prosthetic valve, a cochlear implant or another magnetic or conductive metal which causes a problem in brain MRI imaging.

A participant or a planned participant of a clinical trial of a new therapeutic drug for Alzheimer-type dementia who may participate both in the trial and this trial. An individual who participates in another clinical trial or who has participated within one month.

An individual considered by the principal investigator to be ineligible.

<Intervention>

The components contained in the test foods used for the intervention are shown in Table 1.

*Bifidobacterium* intake group:

Powder (stick)·*Bifidobacterium* 20 billion/stick (2.0 g/day)

Placebo intake group:

Powder (stick)·*Bifidobacterium* 000 million/stick (2.0 g/day)

Intervention period: 24 weeks

TABLE 1

| | Content | |
|---|---|---|
| Composition | *Bifidobacterium* Intake Group | Placebo Intake Group |
| Amount | 2.0 g | 2.0 g |
| Relevant Component | 20 billion cells or more of live *Bifidobacterium* strain MCC1274 | — |
| Additive | Starch | Starch |

<Assessment Items>

(Primary Assessment Item)

ADAS-Jcog. (Alzheimer's Disease Assessment Scale-cognitive component-Japanese version)

(Secondary Assessment Item)

Head MRI (VSRAD: voxel-based specific regional analysis system for Alzheimer's Disease)

(ADAS-Jcog.)

The measured values and the changes (the value at week 24—the value at week 0) of ADAS-Jcog. as the primary assessment item of the FAS (Full Analysis Set) analysis of 115 subjects (55 individuals in the *Bifidobacterium* intake group and 60 individuals in the placebo intake group) are shown in Table 2.

TABLE 2

| ADAS-Jcog. Item | Group | Baseline | Week 8 | Week 16 | Week 24 | P value | Δ Week 24 | P value |
|---|---|---|---|---|---|---|---|---|
| Orientation | Bifidobacterium Intake Group | 0.35 (0.58) | 0.42 (0.74) | 0.35 (0.68) | 0.22 (0.54) | 0.1169 | −0.14 (0.53) | 0.0205* |
| | Placebo Intake Group | 0.37 (0.99) | 0.4 (0.81) | 0.41 (0.88) | 0.47 (0.97) | | 0.16 (0.75) | |

In Table 2, the data are shown with the averages (standard deviations) (*P<0.05, comparison of the changes from the baseline between the groups (the Wilcoxon rank sum test)).

From Table 2, it can be seen that orientation, which is a cognitive function, improved significantly in the *Bifidobacterium* intake group compared to that of the placebo intake group.

(VSRAD)

In the FAS analysis of the head MRI (VSRAD), which is the secondary assessment item, the subjects were 89 individuals (42 individuals in the *Bifidobacterium* intake group and 47 individuals in the placebo intake group).

In Table 3, the measured values and the changes (the value at week 24—the value at week 0) of the VSRAD scores (the Z score in the VOI, the proportion of the entire brain atrophy area, the proportion of the atrophy area in the VOI and the atrophy ratio (inside VOI/entire brain)) are shown.

TABLE 3

| | Group | Baseline | Week 24 | P value | Δ Week 24 | P value |
|---|---|---|---|---|---|---|
| Z Score in VOI | Bifidobacterium Intake Group | 1.21 (0.69) | 1.22 (0.75) | 0.788 | 0.01 (0.17) | 0.357 |
| | Placebo Intake Group | 1.02 (0.6) | 1.04 (0.62) | 0.1488 | 0.02 (0.11) | |
| Proportion of Entire Brain Atrophy Area | Bifidobacterium Intake Group | 3.64 (1.82) | 3.56 (1.63) | 0.398 | −0.07 (0.45) | 0.013 |
| | Placebo Intake Group | 3.56 (1.91) | 3.73 (2.06)* | 0.011 | 0.16 (0.42) | |

TABLE 3-continued

| | Group | Baseline | Week 24 | P value | Δ Week 24 | P value |
|---|---|---|---|---|---|---|
| Proportion of Atrophy Area in VOI | Bifidobacterium Intake Group | 15.98 (20.76) | 16.41 (21.78) | 0.694 | 0.43 (4.99) | 0.527 |
| | Placebo Intake Group | 9.75 (19.04) | 10.74 (19.97)† | 0.081 | 0.98 (2.45) | |
| Atrophy Ratio (Inside VOI/ Entire Brain) | Bifidobacterium Intake Group | 3.97 (4.39) | 3.98 (4.4) | 0.743 | 0.01 (1.33) | 0.97 |
| | Placebo Intake Group | 2.5 (4.25) | 2.74 (4.41) | 0.499 | 0.24 (0.95) | |

In Table 3, the data are shown with the averages (standard deviations) (†P<0.1, *P<0.05, the changes from the baseline (the Wilcoxon signed-rank test)).

VOI, Volume Of Interest

In Table 4, the results of a subgroup analysis based on the Z scores in the VOI at week 0 are shown.

TABLE 4

| | Group | | Baseline | Week 24 | Δ Week 24 | P value |
|---|---|---|---|---|---|---|
| Subgroup: Z score in VOI ≥ 1.0 | | | | | | |
| Z Score in VOI | *Bifidobacterium* Intake Group | n = 22 | 1.69 (0.62) | 1.72 (0.71) | 0.02 (0.22) | 0.0862 |
| | Placebo Intake Group | n = 16 | 1.61 (0.69) | 1.7 (0.67) * | 0.09 (0.12) | |
| Proportion of Entire Brain Atrophy Area | *Bifidobacterium* Intake Group | n = 22 | 4.3 (2.14) | 4.15 (1.8) | −0.15 (0.51) | 0.0565 |
| | Placebo Intake Group | n = 16 | 4 (2.15) | 4.16 (2.34) | 0.16 (0.44) | |
| Proportion of Atrophy Area in VOI | *Bifidobacterium* Intake Group | n = 22 | 29.32 (21.12) | 29.86 (22.84) | 0.54 (6.86) | 0.0546 |
| | Placebo Intake Group | n = 16 | 26.57 (25.54) | 29.58 (25.41) ** | 3 (3.26) | |
| Atrophy Ratio (Inside VOI/Entire Brain) | *Bifidobacterium* Intake Group | n = 22 | 7.11 (3.92) | 7.09 (3.98) | −0.02 (1.83) | 0.2871 |
| | Placebo Intake Group | n = 16 | 6.6 (5.28) | 7.41 (4.9) * | 0.81 (1.44) | |
| Subgroup: Z score in VOI < 1.0 | | | | | | |
| Z Score in VOI | *Bifidobacterium* Intake Group | n = 20 | 0.68 (0.21) | 0.67 (0.26) | −0.01 (0.1) | 0.9230 |
| | Placebo Intake Group | n = 31 | 0.71 (0.14) | 0.7 (0.16) | −0.01 (0.1) | |
| Proportion of Entire Brain Atrophy Area | *Bifidobacterium* Intake Group | n = 20 | 2.91 (1.02) | 2.93 (1.14) | 0.02 (0.42) | 0.1180 |
| | Placebo Intake Group | n = 31 | 3.34 (1.76) | 3.5 (1.89)† | 0.16 (0.42) | |
| Proportion of Atrophy Area in VOI | *Bifidobacterium* Intake Group | n = 20 | 1.31 (2) | 1.62 (2.73) | 0.31 (0.76) | 0.3834 |
| | Placebo Intake Group | n = 31 | 1.07 (1) | 1.01 (1.28) | −0.06 (0.76) | |
| Atrophy Ratio (Inside VOI/Entire Brain) | *Bifidobacterium* Intake Group | n = 20 | 0.52 (0.83) | 0.56 (0.89) | 0.05 (0.26) | 0.4043 |
| | Placebo Intake Group | n = 31 | 0.39 (0.38) | 0.32 (0.41) | −0.06 (0.26) | |

In Table 4, the data are shown with the averages (standard deviations) (†P<0.1, *P<0.05, **P<0.01, the changes from the baseline (the Wilcoxon signed-rank test)).

Figure 2:
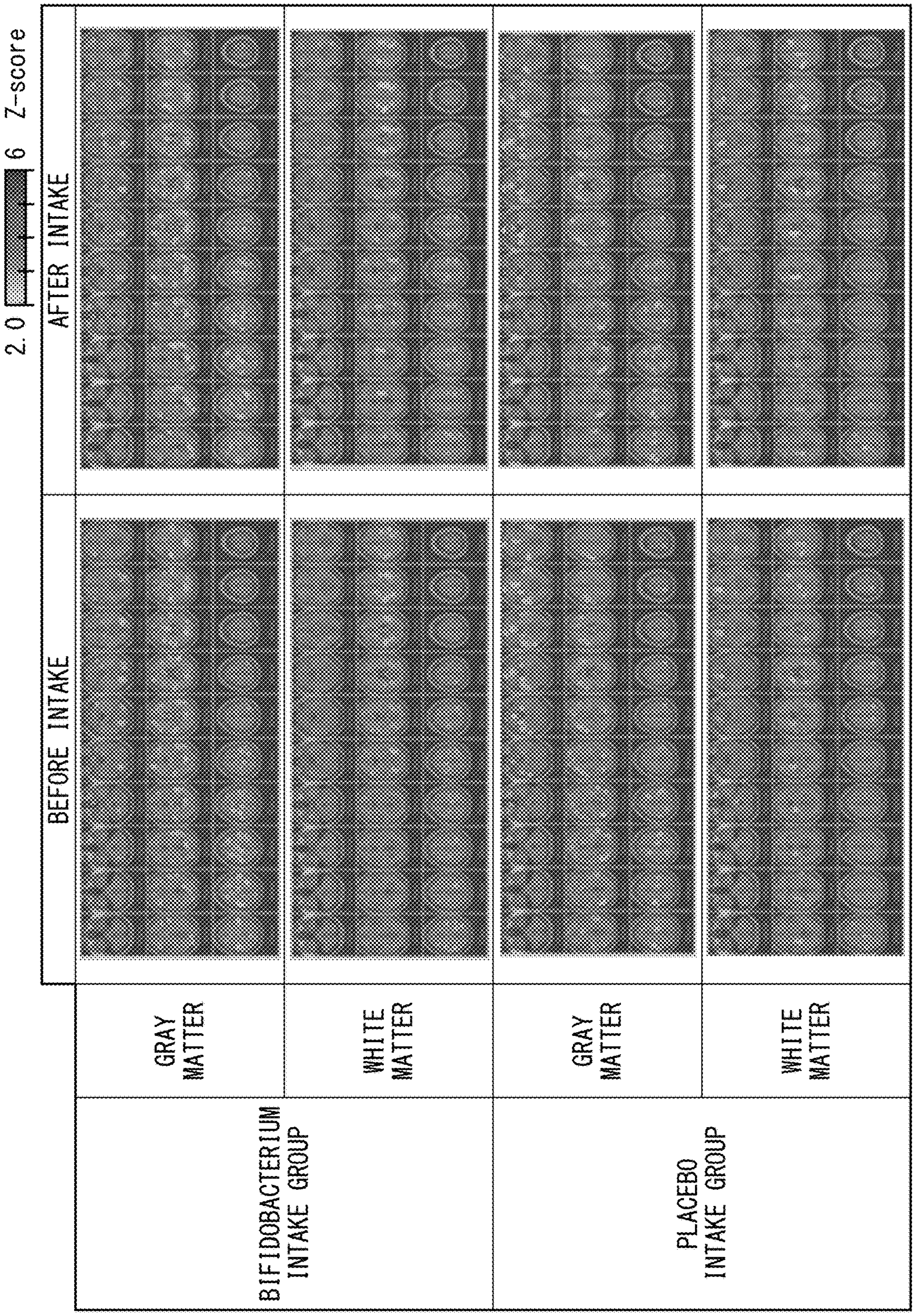
FIG. 2 shows typical MRI images of the subjects (A: *Bifidobacterium* intake group, B: placebo intake group).

FIG. 1 shows the results showing the changes in the VSRAD scores of the subjects, and FIG. 2 shows typical MRI images.

For VSRAD, the brain area in which atrophy specific in dementia such as Alzheimer's disease is found is set as the VOI, and the degree of brain atrophy of the subject can be assessed by comparing with the standardized brain volume data of 80 healthy adults aged 54 to 86 years. Accordingly, from the data, it was found that the intake of the *Bifidobacterium* improved the proportion of the entire brain atrophy area in the FAS analysis and improved all of the Z score in the VOI, the proportion of the entire brain atrophy area and the proportion of the atrophy area in the VOI in the subgroup analysis using individuals who had advanced atrophy in the VOI from the beginning (Z score in the VOI of 1 or more) as the subjects.

The summary of the above trial results is as follows.

By taking 2.0 g (20 billion cells) of *Bifidobacterium breve* MCC1274 (FERM BP-11175) per day for 24 weeks, the proportion of the entire brain atrophy area improved, and in addition, brain atrophy in the VOI area including the hippocampus, the parahippocampal gyrus and the tonsils, in which atrophy is found especially in dementia, improved.

Moreover, improvement of orientation was observed in the neuropsychological testing. Orientation is the ability of understanding the situation of the individual such as the date, the time, the place and the persons in the surroundings, and it is known that multiple brain areas including the hippocampus are responsible for its functions. Moreover, orientation is known as a highly sensitive cognitive area for assessing transition from MCI to dementia. Accordingly, it was suggested that *Bifidobacterium breve* MCC1274 (FERM BP-11175) suppresses brain atrophy and thus suppresses a decline of cognitive functions such as orientation.

INDUSTRIAL APPLICABILITY

According to this disclosure, a brain atrophy suppressor which can suppress the progress of brain atrophy in a subject selected from an individual diagnosed with mild cognitive impairment and a subject at a risk of at least one of cognitive decline and a neurodegenerative disease can be provided. The active ingredient of the brain atrophy suppressor of this disclosure is a culture containing *Bifidobacterium breve* MCC1274 (FERM BP-11175), and thus the brain atrophy suppressor is highly safe, is not likely to cause need for worries for side effects even after long-term continuous administration and is thus very useful.

This disclosure includes the following contents without limitation.

[1] A brain atrophy suppressor containing a culture containing *Bifidobacterium breve* MCC1274 (FERM BP-11175) as an active ingredient which is administered to a subject selected from a healthy individual, an individual diagnosed with mild cognitive impairment, an individual assessed as having cognitive decline and a subject at a risk of a neurodegenerative disease.

[2] The brain atrophy suppressor described in [1] in which the brain atrophy suppressor contains the culture in such an amount that $1.0\times10^9$ to $1.0\times10^{11}$ CFU of the *Bifidobacterium breve* MCC1274 (FERM BP-11175) is orally administered per day to the subject.

[3] The brain atrophy suppressor described in [1] or [2] in which the subject is an individual diagnosed with mild cognitive impairment.

[4] A method for suppressing brain atrophy including administering a culture containing *Bifidobacterium breve* MCC1274 (FERM BP-11175) in an effective amount for suppressing brain atrophy to a subject selected from a healthy individual in need of suppression of brain atrophy, an individual diagnosed with mild cognitive impairment, an individual assessed as having cognitive decline and a subject at a risk of a neurodegenerative disease.

[5] A non-therapeutic method for suppressing brain atrophy including administering a culture containing *Bifidobacterium breve* MCC1274 (FERM BP-11175) in an effective amount for suppressing brain atrophy to a subject selected from a healthy individual in need of suppression of brain atrophy, an individual diagnosed with mild cognitive impairment and a subject at a risk of cognitive decline or a neurodegenerative disease.

[6] The method for suppressing brain atrophy described in [4] or [5] in which the effective amount for suppressing brain atrophy is such an amount that $1.0\times10^9$ to $1.0\times10^{11}$ CFU of the *Bifidobacterium breve* MCC1274 (FERM BP-11175) is orally administered per day to the subject.

[7] The method for suppressing brain atrophy described in any one of [4] to [6] in which the subject is an individual diagnosed with mild cognitive impairment.

[8] A culture containing *Bifidobacterium breve* MCC1274 (FERM BP-11175) for use in the suppression of brain atrophy of a subject selected from a healthy individual, an individual diagnosed with mild cognitive impairment, an individual assessed as having cognitive decline and a subject at a risk of a neurodegenerative disease.

[9] The culture described in [8] in which the culture contains the *Bifidobacterium breve* MCC1274 (FERM BP-11175) in such an amount that $1.0\times10^9$ to $1.0\times10^{11}$ CFU of the *Bifidobacterium breve* MCC1274 (FERM BP-11175) is orally administered per day to the subject.

[10] The culture described in [8] or [9] in which the subject is an individual diagnosed with mild cognitive impairment.

[11] Use of a culture containing *Bifidobacterium breve* MCC1274 (FERM BP-11175) for the manufacture of a brain atrophy suppressor which is administered to a subject selected from a healthy individual, an individual diagnosed with mild cognitive impairment, an individual assessed as having cognitive decline and a subject at a risk of a neurodegenerative disease.

[11] The use of a culture containing *Bifidobacterium breve* MCC1274 (FERM BP-11175) described in in which the brain atrophy suppressor contains the *Bifidobacterium breve* MCC1274 (FERM BP-11175) in such an amount that $1.0\times10^9$ to $1.0\times10^{11}$ CFU of the *Bifidobacterium breve* MCC1274 (FERM BP-11175) is orally administered per day to the subject.

[12] The use of a culture containing *Bifidobacterium breve* MCC1274 (FERM BP-11175) described in or in which the subject is an individual diagnosed with mild cognitive impairment.

[13] A brain atrophy suppressor containing a culture containing *Bifidobacterium breve* MCC1274 (FERM BP-11175) as an active ingredient which contains the *Bifidobacterium breve* MCC1274 (FERM BP-11175) in such an amount that $1.0\times10^6$ to $1.0\times10^{12}$ CFU of the *Bifidobacterium breve* MCC1274 (FERM BP-11175) is orally administered per day to a subject selected from a healthy individual, an individual diagnosed with mild cognitive impairment, an individual assessed as having cognitive decline and a subject at a risk of a neurodegenerative disease.

[14] The brain atrophy suppressor described in in which the subject is an individual diagnosed with mild cognitive impairment.

[15] A method for suppressing brain atrophy including orally administering $1.0\times10^6$ to $1.0\times10^{12}$ CFU of *Bifidobacterium breve* MCC1274 (FERM BP-11175) per day as an effective amount for suppressing brain atrophy of a culture containing *Bifidobacterium breve* MCC1274 (FERM BP-11175) to a subject selected from a healthy individual in need of suppression of brain atrophy, an individual diagnosed with mild cognitive impairment, an individual assessed as having cognitive decline and a subject at a risk of a neurodegenerative disease.

[16] A non-therapeutic method for suppressing brain atrophy including orally administering $1.0\times10^6$ to $1.0\times10^{12}$ CFU of *Bifidobacterium breve* MCC1274 (FERM BP-11175) per day as an effective amount for suppressing brain atrophy of a culture containing *Bifidobacterium breve* MCC1274 (FERM BP-11175) to a subject selected from a healthy individual in need of suppression of brain atrophy, an individual diagnosed with mild cognitive impairment, an individual assessed as having cognitive decline and a subject at a risk of a neurodegenerative disease.

[17] The method for suppressing brain atrophy described in [15] or [16] in which the subject is an individual diagnosed with mild cognitive impairment.

[18] A culture containing *Bifidobacterium breve* MCC1274 (FERM BP-11175) for use in the suppression of brain atrophy which contains the *Bifidobacterium breve* MCC1274 (FERM BP-11175) in such an amount that $1.0\times10^6$ to $1.0\times10^{12}$ CFU of the *Bifidobacterium breve* MCC1274 (FERM BP-11175) is orally administered per day to a subject selected from a healthy individual, an individual diagnosed with mild cognitive impairment, an individual assessed as having cognitive decline and a subject at a risk of a neurodegenerative disease.

[19] The culture described in [18] in which the subject is an individual diagnosed with mild cognitive impairment.

[20] A food or a drink containing a culture containing *Bifidobacterium breve* MCC1274 (FERM BP-11175) which is labeled with a brain atrophy-suppressing effect on a subject selected from a healthy individual, an individual diagnosed with mild cognitive impairment, an individual assessed as having cognitive decline and a subject at a risk of a neurodegenerative disease.

[21] The food or the drink described in [20] in which the food or the drink contains the culture in such an amount that $1.0\times10^9$ to $1.0\times10^{11}$ CFU of the *Bifidobacterium breve* MCC1274 (FERM BP-11175) is taken per day by the subject.

[22] The food or the drink described in [20] or [21] in which the subject is an individual diagnosed with mild cognitive impairment.

[23] A food for suppressing brain atrophy containing a culture containing *Bifidobacterium breve* MCC1274 (FERM BP-11175) as an active ingredient which is taken by a subject selected from a healthy individual, an individual diagnosed with mild cognitive impairment, an individual assessed as having cognitive decline and a subject at a risk of a neurodegenerative disease.

[24] The food for suppressing brain atrophy described in [23] in which the food for suppressing brain atrophy contains the culture in such an amount that $1.0\times10^9$ to $1.0\times10^{11}$ CFU of the *Bifidobacterium breve* MCC1274 (FERM BP-11175) is taken per day by the subject.

[25] The food for suppressing brain atrophy described in [23] or [24] in which the subject is an individual diagnosed with mild cognitive impairment.

[26] A supplement for suppressing brain atrophy containing a culture containing *Bifidobacterium breve* MCC1274 (FERM BP-11175) as an active ingredient for intake by a subject selected from a healthy individual, an individual diagnosed with mild cognitive impairment, an individual assessed as having cognitive decline and a subject at a risk of a neurodegenerative disease.

[27] The supplement for suppressing brain atrophy described in [26] in which the supplement for suppressing brain atrophy contains the culture in such an amount that $1.0\times10^9$ to $1.0\times10^{11}$ CFU of the *Bifidobacterium breve* MCC1274 (FERM BP-11175) is taken per day by the subject.

[28] The supplement for suppressing brain atrophy described in [24] or [25] in which the subject is an individual diagnosed with mild cognitive impairment.

[29] A medicine for suppressing brain atrophy containing a culture containing *Bifidobacterium breve* MCC1274 (FERM BP-11175) as an active ingredient for administration to a subject selected from a healthy individual, an individual diagnosed with mild cognitive impairment, an individual assessed as having cognitive decline and a subject at a risk of a neurodegenerative disease.

[30] The medicine for suppressing brain atrophy described in [29] in which the medicine for suppressing brain atrophy contains the culture in such an amount that $1.0\times10^9$ to $1.0\times10^{11}$ CFU of the *Bifidobacterium breve* MCC1274 (FERM BP-11175) is orally administered per day to the subject.

[31] The medicine for suppressing brain atrophy described in [29] or [30] in which the subject is an individual diagnosed with mild cognitive impairment.

The invention claimed is:

1. A method for suppressing brain atrophy in a subject in need thereof comprising administering a culture containing *Bifidobacterium breve* MCC1274 (FERM BP-11175) in an effective amount to the subject, wherein the subject is selected from the group consisting of:

(a) a healthy individual in need of suppression of brain atrophy, (b) an individual who has been diagnosed with mild cognitive impairment, (c) an individual who has been assessed as having cognitive decline, and (d) an individual who is at a risk for being diagnosed with a neurodegenerative disease, and (e) combinations thereof, wherein the subject has a Z score of 1 or more as measured by analyzing MRI images of the parahippocampal gyrus, hippocampus, and tonsils of the subject's head by VSRAD.

2. A method of making a composition for suppressing brain atrophy in a subject in need thereof comprising culturing *Bifidobacterium breve* MCC1274 (FERM BP-11175);

wherein said subject is selected from the group consisting of:

(a) a healthy individual who is at risk of brain atrophy, (b) an individual who has been diagnosed with mild cognitive impairment, (c) an individual who has been assessed as having cognitive decline, (d) an individual who is at a risk for a neurodegenerative disease, and (e) combinations thereof, wherein the subject has a Z score of 1 or more as measured by analyzing MRI images of the parahippocampal gyrus, hippocampus, and tonsils of the subject's head by VSRAD.

3. The method of claim 1, wherein said administering occurs orally daily and said *Bifidobacterium breve* MCC1274 (FERM BP-11175) is present in an amount of $1.0\times10^6$ to $1.0\times10^{12}$ CFU.

* * * * *